United States Patent
Sakamoto et al.

(10) Patent No.: US 8,030,342 B2
(45) Date of Patent: Oct. 4, 2011

(54) DENDRITIC POLYAMIDOAMINE PHTHALOCYANINE DERIVATIVE

(75) Inventors: Keiichi Sakamoto, Chiyoda-ku (JP); Seiko Kanazawa, Chiyoda-ku (JP)

(73) Assignee: Nihon University, Tokyo (JP)

( * ) Notice: Subject to any disclaimer, the term of this patent is extended or adjusted under 35 U.S.C. 154(b) by 123 days.

(21) Appl. No.: 12/513,075

(22) PCT Filed: Sep. 13, 2007

(86) PCT No.: PCT/JP2007/001001
§ 371 (c)(1), (2), (4) Date: Apr. 30, 2009

(87) PCT Pub. No.: WO2008/056433
PCT Pub. Date: May 15, 2008

(65) Prior Publication Data
US 2010/0075940 A1 Mar. 25, 2010

(30) Foreign Application Priority Data
Nov. 8, 2006 (JP) ................. 2006-302304

(51) Int. Cl.
*A01N 55/02* (2006.01)
*A61K 31/40* (2006.01)
*C07B 47/00* (2006.01)
*C07D 487/22* (2006.01)
*A61B 5/00* (2006.01)

(52) U.S. Cl. .................. 514/410; 424/9.362; 424/9.61; 540/145; 514/185

(58) Field of Classification Search .................. 540/145; 514/410; 424/9.362, 9.61
See application file for complete search history.

(56) References Cited

U.S. PATENT DOCUMENTS
2003/0170178 A1 9/2003 Roncucci et al.

FOREIGN PATENT DOCUMENTS
| JP | 2000 44565 | 2/2000 |
| JP | 2002 6558 | 1/2002 |
| JP | 2005 120068 | 5/2005 |
| JP | 2005-120068 A | 5/2005 |
| WO | 01 96343 | 12/2001 |

OTHER PUBLICATIONS

Ryo Hirohashi, et al., "Phthalocyanine as a Functional Dye", IPC, 2004, 42 pages, (with partial English translation).
Hirofusa Shirai et al., "Phthalocyanine—Chemistry and Function—" IPC, 1997, 24 pages, (with partial English translation).
Keigo Aoi, et al., "Dendritic Polymers, Tabunki Kozo ga Hirogeru Kokinoka no Sekai (World of High Functionalization Diversified by Multibranched Structures)", NTS, 2005, 14 pages, (with partial English translation).
Shohiko Okada, "Chemistry and Function of Dendrimers", IPC, 2000, 24 pages, (with partial English translation).
"The 2nd Graduate School of Industrial Technology, Nihon University The Advanced Research Center for Life Science and Human Environment Research Announcement Lecture Presentation", Oct. 6, 2006, 9 pages, (with English translation).

Primary Examiner — Paul V. Ward
(74) Attorney, Agent, or Firm — Oblon, Spivak, McClelland, Maier & Neustadt, L.L.P.

(57) ABSTRACT

The present invention is directed to a dendritic polyamidoamine phthalocyanine derivative which is useful as, for example, a fluorescent material or a photodynamic therapeutic drug for cancer. The derivative is represented by the following formula (1):

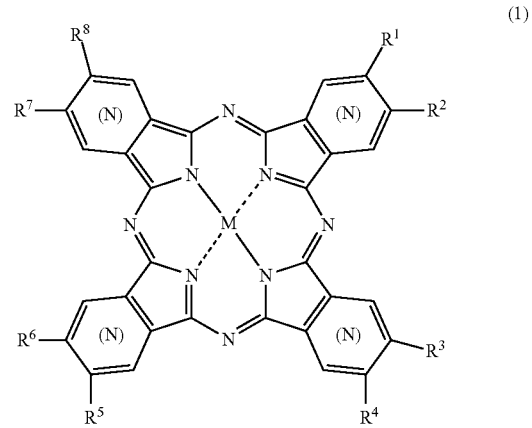

(wherein each member of one to eight of $R^1$ to $R^8$ is a polyamidoamine dendron represented by the following formula (a):

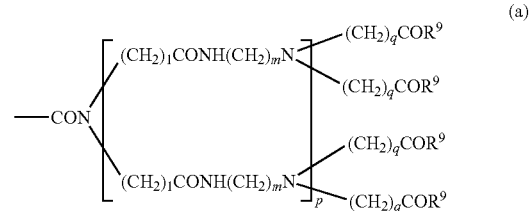

(wherein p is a number from 1 to 4; $R^9$ represents —NH$(CH_2)_r$NH$_2$ or OR$^{10}$ (wherein R$^{10}$ represents an alkyl group); and each of l, m, q, and t is a number from 1 to 8), and each member of the remainder represents a hydrogen atom; M represents a metal atom having a valency of two or more; and a ring marked with (N) is a benzene ring, a pyridine ring, or a pyrazine ring).

16 Claims, 4 Drawing Sheets

DENDRITIC POLYAMIDOAMINE PHTHALOCYANINE DERIVATIVE

CROSS-REFERENCE TO RELATED APPLICATIONS

This application is a 371 of PCT/JP07/001,001 filed Sep. 13, 2007 and claims the benefit of JP 2006-302304 filed Nov. 8, 2006.

TECHNICAL FIELD

The present invention relates to a dendritic polyamidoamine phthalocyanine derivative which is useful as, for example, a fluorescent material or a photodynamic therapeutic drug for cancer.

BACKGROUND ART

Phthalocyanine is a compound which, in its center, can coordinate to a metal, expresses a blue to green color, and exhibits various optical characteristics (e.g., selective absorption of visible light of 600 nm to 700 nm). Therefore, phthalocyanine is envisaged to be applied in a variety of fields, including light-emitting materials, fluorescent materials, and photodynamic therapeutic drugs for cancer, and many derivatives of phthalocyanine have been synthesized (Non-Patent Documents 1 and 2).

Meanwhile, a dendrimer is a dendritic molecule having a branching structure formed of repeating units. When a dendrimer is bonded to a compound serving as a core, the entire molecule assumes a spherical form. Dendrimers are envisaged to be used as, for example, optoelectronic materials, by virtue of their characteristics such as solubility, low viscosity, and amorphousness (Non-Patent Documents 3 and 4).

As has been reported, a phthalocyanine derivative serving as a photosensitizer can be used as a core of a dendrimer (Patent Document 1). However, since this phthalocyanine dendrimer has an aromatic ether dendron unit, the entire dendrimer molecule assumes a spherical form and loses intrinsic optical characteristics acquired by a phthalocyanine structure.

Patent Document 1: JP-A-2005-120068
Non-Patent Document 1: Ryo Hirohashi, Keiichi Sakamoto, and Eiko Okumura "Phthalocyanine as a Functional Dye" IPC, 2004
Non-Patent Document 2: Hirofusa Shirai and Nagao Kobayashi "Phthalocyanine—Chemistry and Function—" IPC, 1997
Non-Patent Document 3: Keigo Aoi and Masaaki Kakimoto "Dendritic Polymers, Tabunki Kozo ga Hirogeru Kokinoka no Sekai (World of High Functionalization Diversified by Multibranched Structures)" NTS, 2005
Non-Patent Document 4: Shohiko Okada "Chemistry and Function of Dendrimers" IPC, 2000

DISCLOSURE OF THE INVENTION

Problems to be Solved by the Invention

An object of the present invention is to provide a novel compound which retains optical characteristics of phthalocyanine serving as a core and exhibits dendrimer characteristics.

Means for Solving the Problems

The present inventors have conducted extensive studies on introduction of a dendron into a phthalocyanine skeleton, and as a result have found that when the benzene ring of an indole structure of a phthalocyanine skeleton is bonded not to an aromatic-group-containing dendron, but to a polyamidoamine dendron of 1st- to 4th-generation, the resultant compound, which is a dendrimer, exhibits intrinsic optical characteristics of phthalocyanine, and the compound is useful as a fluorescent material or a photodynamic therapeutic drug for cancer. The present invention has been accomplished on the basis of this finding.

Accordingly, the present invention provides a dendritic polyamidoamine phthalocyanine derivative represented by the following formula (1):

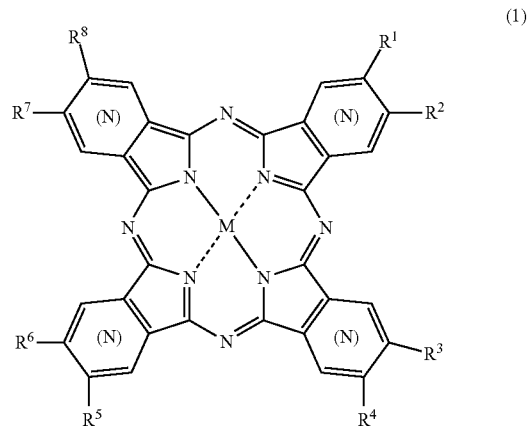

(wherein 1 to 8 members among $R^1$ to $R^8$ are respectively polyamidoamine dendron represented by the following formula (a):

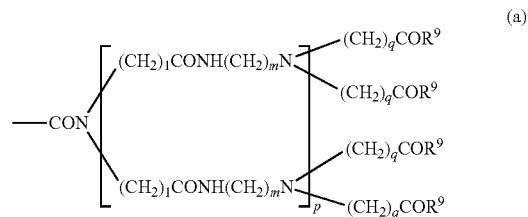

(wherein p is a number from 1 to 4; $R^9$ represents —NH$(CH_2)_t NH_2$ or $OR^{10}$ (wherein $R^{10}$ represents an alkyl group); and each of l, m, q, and t is a number from 1 to 8), and the remaining member(s) represent(s) a hydrogen atom; M represents a metal atom having a valency of two or more; and a ring having (N) is a benzene ring, a pyridine ring, or a pyrazine ring).

The present invention also provides a fluorescent material or a photodynamic therapeutic drug for cancer, which contains the dendritic polyamidoamine phthalocyanine derivative.

The present invention also provides a pharmaceutical composition including the dendritic polyamidoamine phthalocyanine derivative and a pharmaceutically acceptable carrier.

The present invention also provides a use of the dendritic polyamidoamine phthalocyanine derivative for producing a photodynamic therapeutic drug.

The present invention also provides a method of photodynamic therapy including administering an effective amount of the dendritic polyamidoamine phthalocyanine derivative to a subject in need thereof.

Effects of the Invention

The dendrimer of the present invention exhibits optical characteristics of phthalocyanine, which is a core compound, and also exhibits dendrimer characteristics. Therefore, the dendrimer of the present invention is useful as an optical material such as a fluorescent material, or as a photosensitizer such as a photodynamic therapeutic drug for cancer.

BEST MODE FOR CARRYING OUT THE INVENTION

Figure 1:
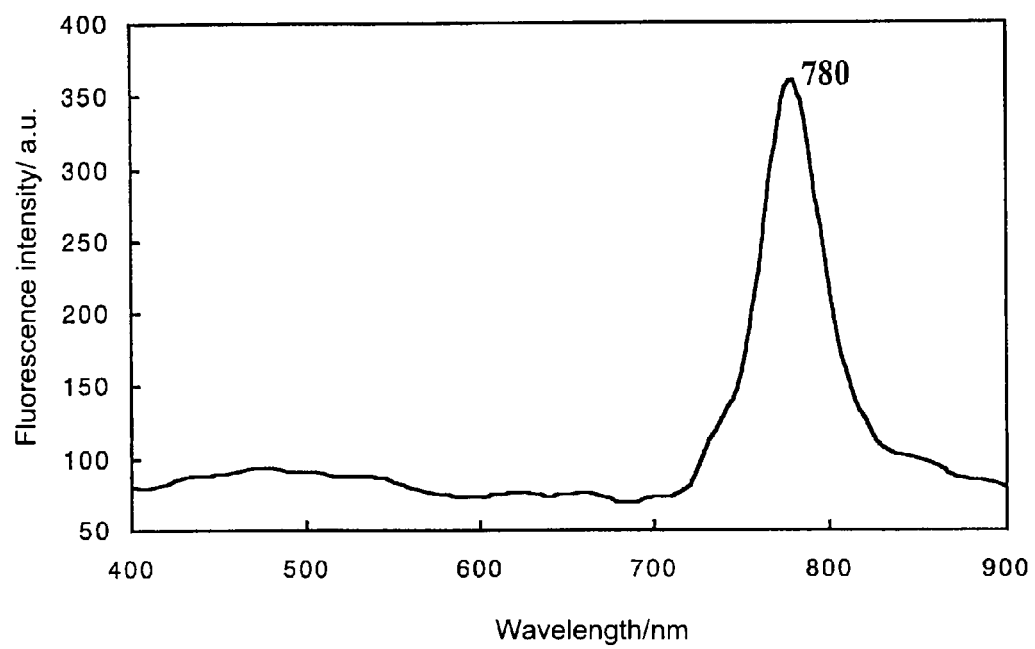
FIG. 1 shows a fluorescence spectrum of G1.0 dendritic PC.

The dendrimer of the present invention has a structure represented by formula (1), wherein 1 to 8 members among $R^1$ to $R^8$ on the phthalocyanine skeleton are respectively polyamidoamine dendron represented by formula (a), and the remaining member(s) is(are) a hydrogen atom. In formula (a), p is a number from 1 to 4, and this number determines the generation of the dendron. The generation number (p) of the dendron is 1 to 4, particularly preferably 1 to 3, from the viewpoint of retaining optical characteristics of phthalocyanine. When the generation number (p) exceeds 4, the branching structure of the dendron becomes large, and phthalocyanine serving as a core tends to lose its optical characteristics.

In formula (a), each of l, m, q, and t of alkylene chains is 1 to 8, preferably 1 to 6, more preferably 2 to 6, particularly preferably 2 to 4. $R^{10}$ represents an alkyl group and is preferably a C1-C8 linear or branched alkyl group such as methyl, ethyl, n-propyl, isopropyl, or tert-butyl. $R^9$ has more preferably an amino-terminal structure; i.e., —NH$(CH_2)_t$NH$_2$.

One to eight members (particularly preferably four to eight) among $R^1$ to $R^8$ are respectively a dendron represented by formula (a). Particularly preferred is the case where four members among $R^1$ to $R^8$ (i.e., $R^1$ or $R^2$, $R^3$ or $R^4$, $R^5$ or $R^6$, and $R^7$ or $R^8$) are respectively a dendron of formula (a), or the case where eight members among $R^1$ to $R^8$ are respectively a dendron of formula (a).

No particular limitation is imposed on the metal atom M, so long as it has a valency of two or more. However, from the viewpoint of fluorescence emission, the metal atom M is preferably, for example, Zn, Mg, or Mn. Particularly, Zn is preferred, from the viewpoints of singlet oxygen generation and high energy level at a photoexcited state.

The ring having (N) may be a benzene ring, a pyridine ring, or a pyrazine ring, but is preferably a benzene ring.

The dendrimer (1) of the present invention may be produced according to, for example, the following reaction scheme:

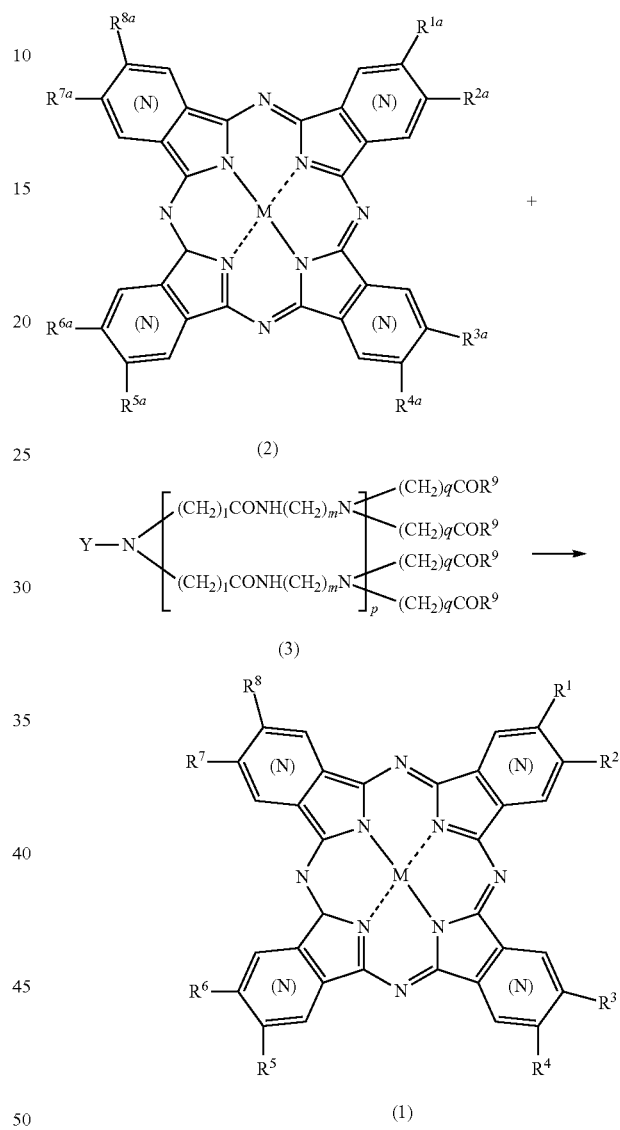

(wherein 1 to 8 members among $R^{1a}$ to $R^{8a}$ represents carboxyl group, and the remaining member(s) represents a hydrogen atom; Y represents an amino-protective group; and $R^1$ to $R^8$, M, l, m, p, q, and $R^9$ have the same meanings as defined above).

Specifically, the dendrimer (1) (i.e., compound represented by formula (1)) may be produced through condensation between a phthalocyanine compound (2) having one to eight carboxyl groups and a polyamidoamine dendron (3).

The phthalocyanine compound (2) having a carboxyl group(s) is obtained by heating urea, and trimellitic anhydride, pyromellitic dianhydride, or a mixture of trimellitic anhydride and phthalic anhydride in the presence of a metal salt.

The dendron of formula (3) may be produced according to, for example, the following reaction scheme:

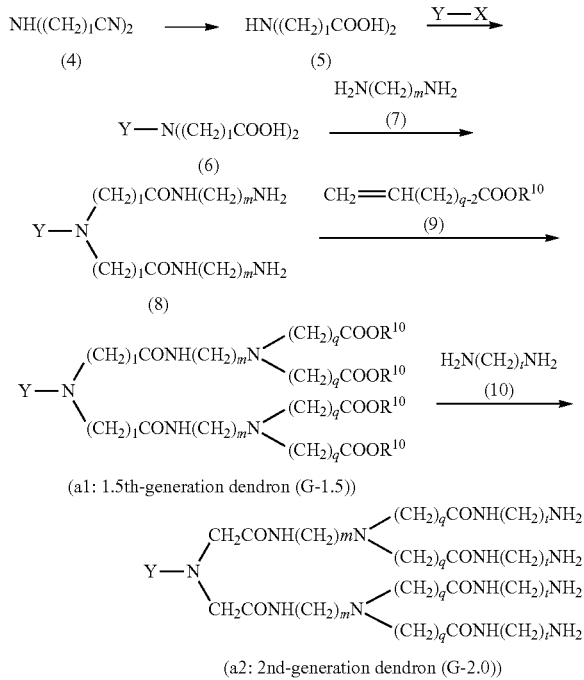

(wherein Y—X represents a reagent for introducing an amino-protective group; and l, m, q, t, and Y have the same meanings as defined above).

Y may be, for example, a t-butoxycarbonyl group (t-Boc), a benzyloxycarbonyl group, or a 9-fluorenylmethoxycarbonyl group. Y—X may be, for example, t-Boc anhydride in the case where Y is t-Boc.

An imidinodialkanonitrile (4) is hydrolyzed with, for example, concentrated hydrochloric acid, to thereby yield an imidinodialkanoic acid (5). Subsequently, the amino group of the thus-obtained compound (5) is protected to form a compound (6), and the compound (6) is reacted with a diamine (7), to thereby yield a compound (8). The compound (8) is reacted with an unsaturated carboxylic acid ester (9), to thereby yield an ester-type dendron (a1). When the dendron (a1) is reacted with a diamine (10), an amino-terminal dendron (a2) is obtained. When the dendron (a2) is further reacted with the unsaturated carboxylic acid ester (9) and the diamine (10), a 3rd-generation dendron is obtained.

Condensation reaction between the phthalocyanine compound (2) having a carboxyl group(s) and the dendron (3) may be carried out in the presence of, for example, an acid. Examples of the acid employed include hydrochloric acid, N-ethyl-, N'-3-dimethylaminocarbodiimide hydrochloride, and benzotriazol-1-yl-tris(dimethylamino)phosphonium. Reaction may be carried out at room temperature to 100° C. for 5 to 72 hours.

The thus-produced dendrimer (1) of the present invention has a dendrimer of 1st- to 4th-generation, and the dendron is a relatively linear polyamidoamine dendron. Therefore, since phthalocyanine serving as a core is not sterically hindered, the dendrimer exhibits optical characteristics of phthalocyanine. Also, the dendrimer (1) of the present invention exhibits dendrimer characteristics, including bioaffinity, visible-light-capturing property, infrared-light-capturing function, function as an electron transfer medium, function as an electron donor, molecular recognition function, biosensor function, DNA vector biointerface function, and drug delivery function.

Thus, the dendrimer (1) of the present invention exhibits high bioaffinity and is useful as, for example, a photodynamic therapeutic drug or a DNA vector. Since phthalocyanine itself is useful as a photodynamic therapeutic drug for cancer, the dendrimer exhibits high specificity to cancer and is useful as a photodynamic therapeutic drug for cancer.

The dendrimer (1) of the present invention exhibits fluorescence characteristics of phthalocyanine and also exhibits fluorescence characteristics based on a polyamidoamine structure. Therefore, the dendrimer is useful as an optical material, particularly as a fluorescent material.

When the dendrimer (1) of the present invention is employed as a drug, the dendrimer may be mixed with a pharmaceutically acceptable carrier, to thereby prepare a variety of drug products (pharmaceutical compositions). Examples of the pharmaceutically acceptable carrier include carriers for injection, such as physiological saline and a buffer; and additives for oral administration, such as an excipient, a disintegrant, and a lubricant. Examples of dosage forms of the drug include intravenous administration, intramuscular administration, subcutaneous administration, topical administration, oral administration, intrarectal administration, and transdermal administration.

When the dendrimer (1) of the present invention or a pharmaceutical composition containing the dendrimer (1) is employed for photodynamic therapy, the dendrimer (1) or the dendrimer-containing pharmaceutical composition is administered to a subject in need thereof through a customary method, followed by irradiation with light.

When the dendrimer (1) of the present invention is employed as an optical material, the dendrimer may be used as a solid prepared through, for example, spin coating, vacuum deposition, photoresist treatment, or photoetching, or as a liquid prepared by dispersing the dendrimer into a solution.

EXAMPLES

The present invention will next be described in more detail by way of examples, which should not be construed as limiting the invention thereto.

Example 1

(i) Synthesis of 3,3'-iminodipropionic acid

For synthesis of 3,3'-iminodipropionic acid, 3,3'-iminodipropionitrile (12 g) was added to concentrated hydrochloric acid (50 mL) and refluxed for 48 hours. Acetone (300 mL) was added to the resultant product, and the mixture was subjected to filtration, followed by drying. The crude product was recrystallized from hot water.

(ii) Synthesis of N-(t-Boc)iminodipropionic acid

For synthesis of N-(t-Boc)iminodipropionic acid, 3,3'-iminodipropionic acid (80 g) was dissolved in pure water (50 mL); 1,4-dioxane (100 mL), an aqueous sodium carbonate solution (50 mmol/50 mL), and triethylamine (15 mL) were added to the solution; the mixture was stirred in an ice bath for one hour; and (t-Boc)$_2$ anhydride (13 g) was gradually added to the mixture at room temperature, followed by stirring for 48 hours. The pH of the resultant mixture was adjusted to about 3 with saturated aqueous citric acid solution, and the mixture was subjected to extraction with ethyl acetate. The organic layer was washed, dehydrated, and concentrated by evaporator. The crude product was recrystallized from a solution of ethyl acetate and hexane (v/v=1/1).

(iii) Synthesis of 1.5th-Generation Dendron

For synthesis of a 1.5th-generation dendron (G-1.5), N-(t-Boc)iminodipropionic acid (2.6 g) dissolved in methanol (20 mL) and ethylenediamine (30 g) dissolved in methanol (100 mL) were stirred in an ice bath for one hour, followed by further stirring at room temperature for 96 hours. Methanol was removed from the resultant mixture by evaporator, and then ethylenediamine was removed through distillation under reduced pressure.

(iv) Synthesis of 2nd-Generation Dendron

For synthesis of a 2nd-generation dendron (G-2), the above-obtained G-1.5 was dissolved in methanol (200 mL); methyl acrylate (8.6 g) was added to the solution; and the mixture was stirred in an ice bath for one hour, followed by further stirring at room temperature for 48 hours. Methanol and methyl acrylate were removed from the resultant mixture through distillation under reduce pressure.

(v) Synthesis of Zinc Phthalocyanine Tetracarboxylic Acid (Hereinafter phthalocyanine May be Abbreviated as "PC")

For synthesis of zinc PC tetracarboxylic acid, trimellitic anhydride (2.2 g), urea (13 g), zinc chloride (3 g), and 1,8-diazabicyclo[5.4.0]undecene (DBU) were added to 1,2,4-trichlorobenzene (50 mL), and the mixture was heated at 250° C. for four hours. The resultant mixture was washed with 6M hydrochloric acid, pure water, and acetone, and then the mixture was filtered. After drying, the resultant solid was added to pure water (90 mL) together with potassium hydroxide (30 g), and hydrolysis was carried out at 100° C. for eight hours. The hydrolyzed mixture was added to pure water (200 mL), and the pH thereof was adjusted to 2 with hydrochloric acid, followed by centrifugation, to thereby yield a solid. The solid was washed with pure water and acetone and then dried. A dendrimer produced by using the thus-synthesized compound as a raw material will be called "type 1."

In a manner similar to that described above, zinc phthalocyanine monocarboxylic acid was synthesized by use of a mixture of trimellitic anhydride and phthalic anhydride (1:3).

(vi) Synthesis of Zinc Phthalocyanine (PC) Octacarboxylic Acid

For synthesis of zinc PC octacarboxylic acid, pyromellitic dianhydride (2.5 g), urea (13 g), zinc chloride (3 g), and DBU were added to 1,2,4-trichlorobenzene (50 mL), and the mixture was heated at 250° C. for four hours. The subsequent treatment was carried out in a manner similar to that described above in synthesis of zinc PC tetracarboxylic acid. A dendrimer produced by using the thus-synthesized compound as a raw material will be called "type 2."

(vii) Synthesis of Dendritic Phthalocyanine (PC)

For synthesis of dendritic PC, G-2 (6.79 g) was dissolved in methanol (30 mL); hydrochloric acid (10 mL) was added to the solution; stirring of the mixture was carried out for one hour; zinc PC octacarboxylic acid (0.94 g) was added to the mixture; and stirring of the mixture was carried out for 48 hours. The resultant product was filtered and then washed with pure water, followed by drying. The above procedure was repeated, except that different types of dendron and carboxylated PC were employed, to thereby synthesize the below-described dendrimers. In the following formulas, "type 1" and "type 2" correspond to the aforementioned phthalocyanine compounds, and "G1.0," "G1.5," or "G2" represents the generation number of the corresponding dendrimer.

Type 1-G1.0 monoamidoamine employed in Example 2 is a 1st-generation dendrimer produced by using zinc PC monocarboxylic acid as a raw material.

[F5]

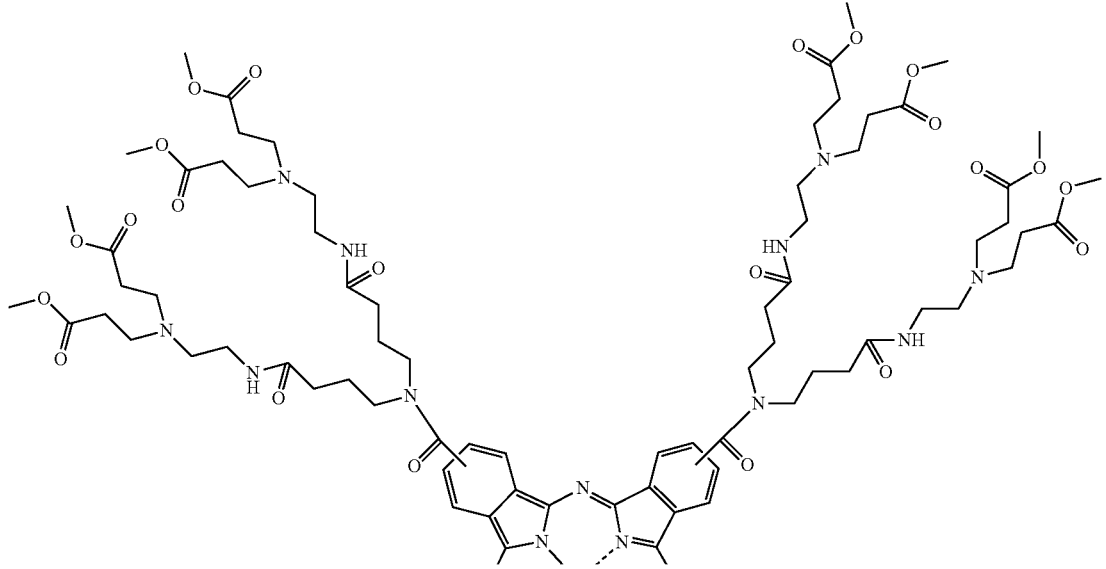

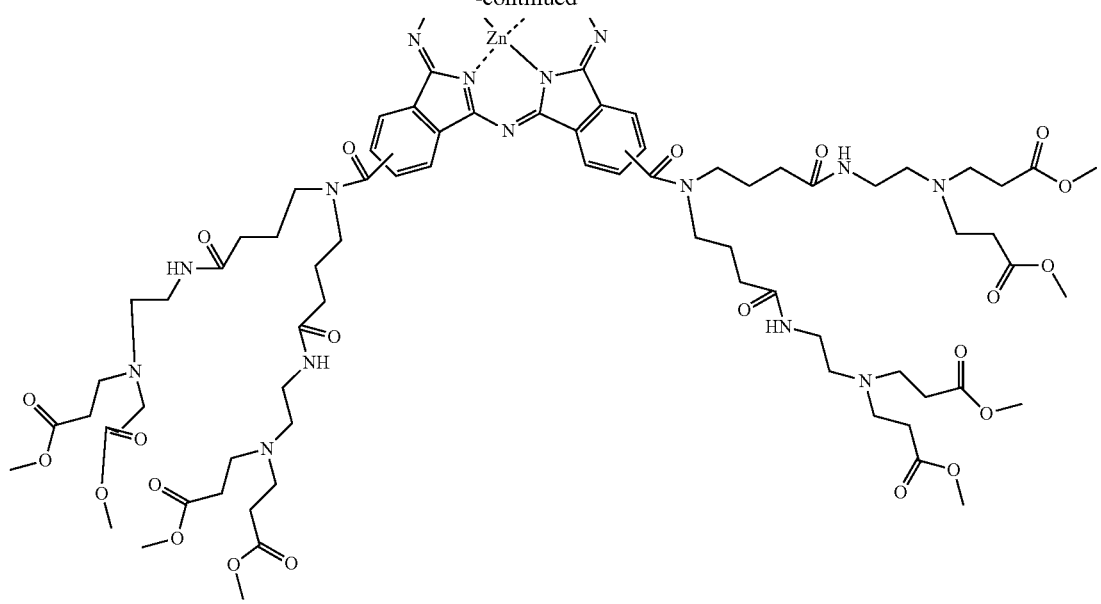
(type 1-G1.5)
Yield 55%
Dark green powdery solid
[F6]
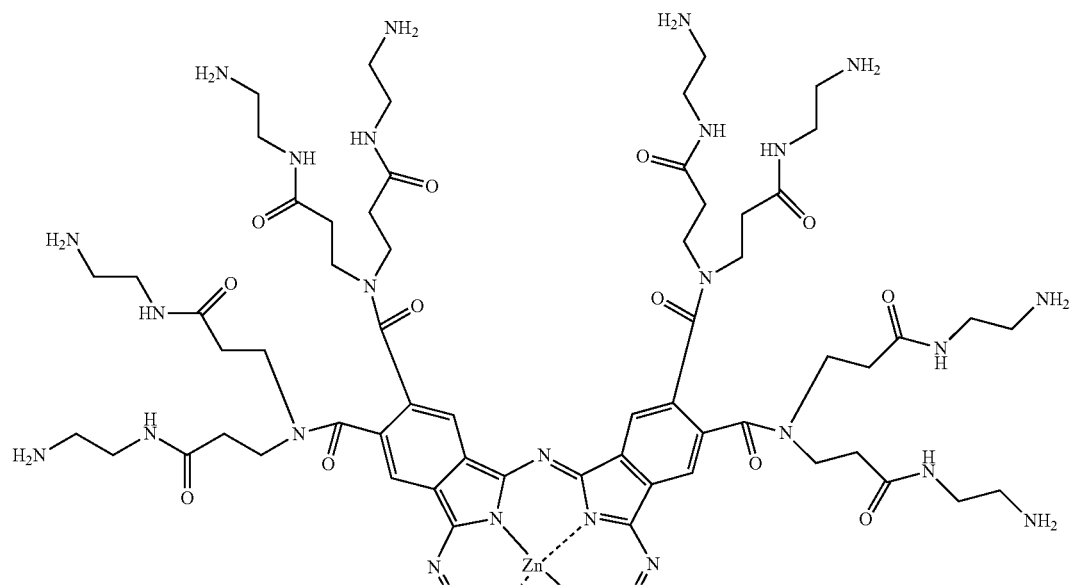

-continued
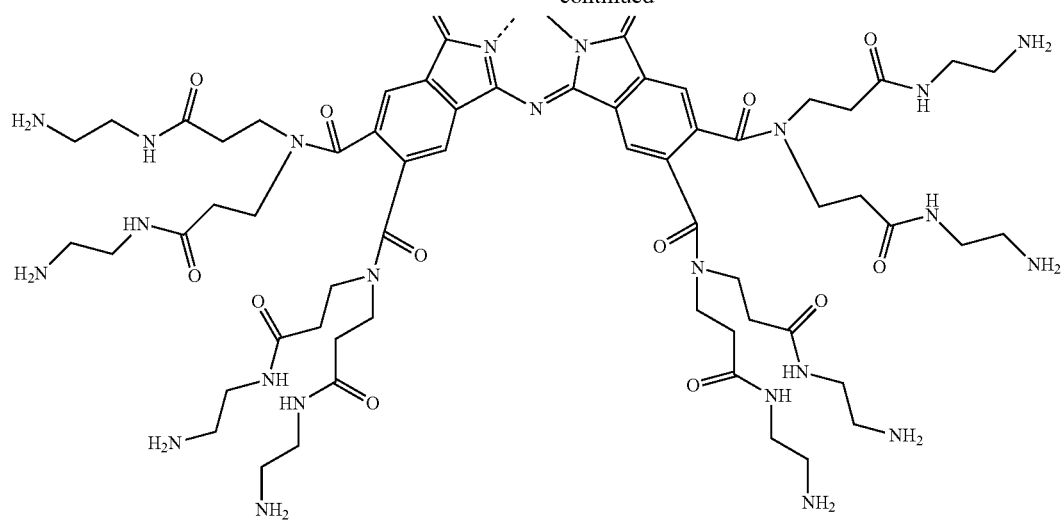
(type 2-G1.0)
Yield 5.55%
Blackish green powdery solid
[F7]
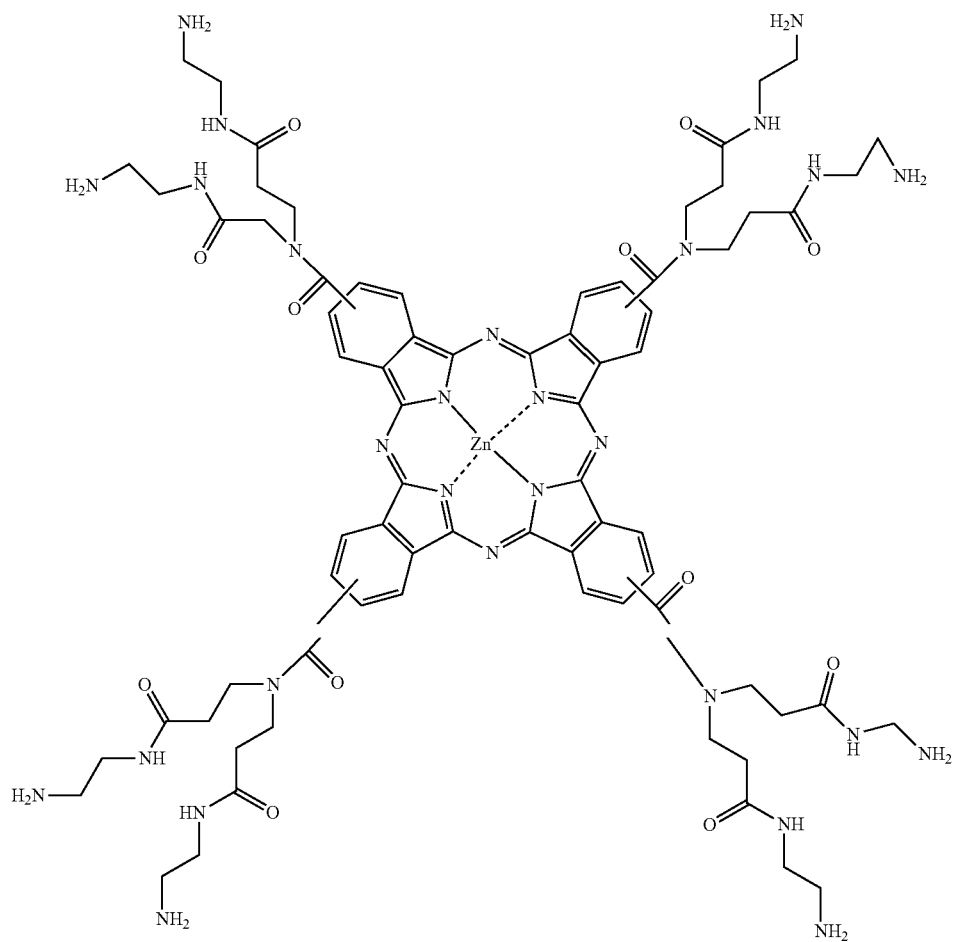

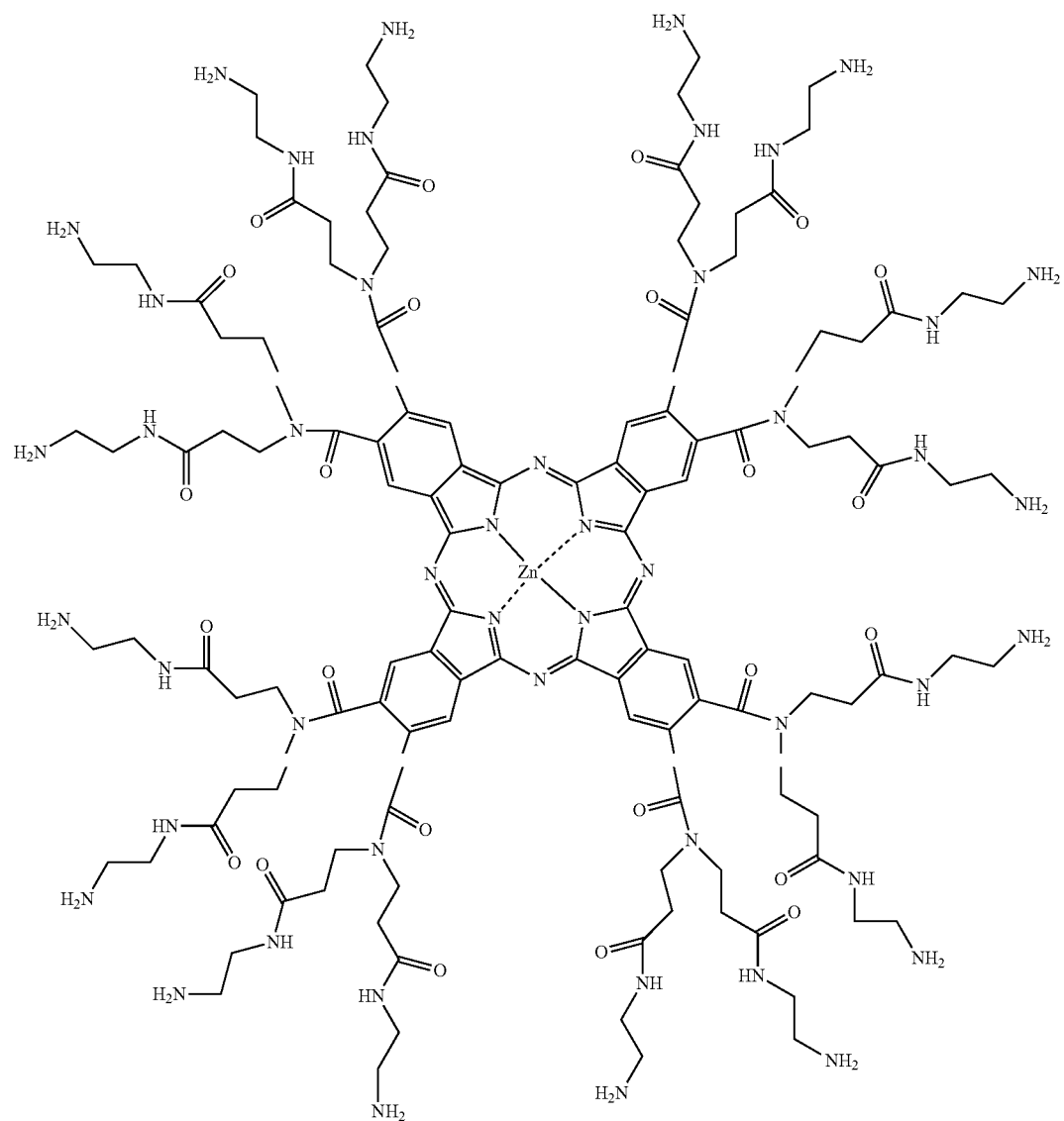
(type 2-G1.0)
Yield 5.55%
Blackish green powdery solid
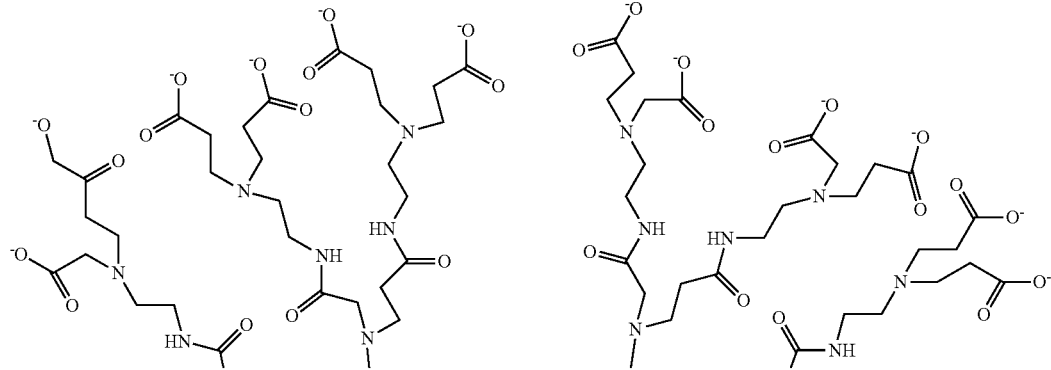
[F8]

-continued

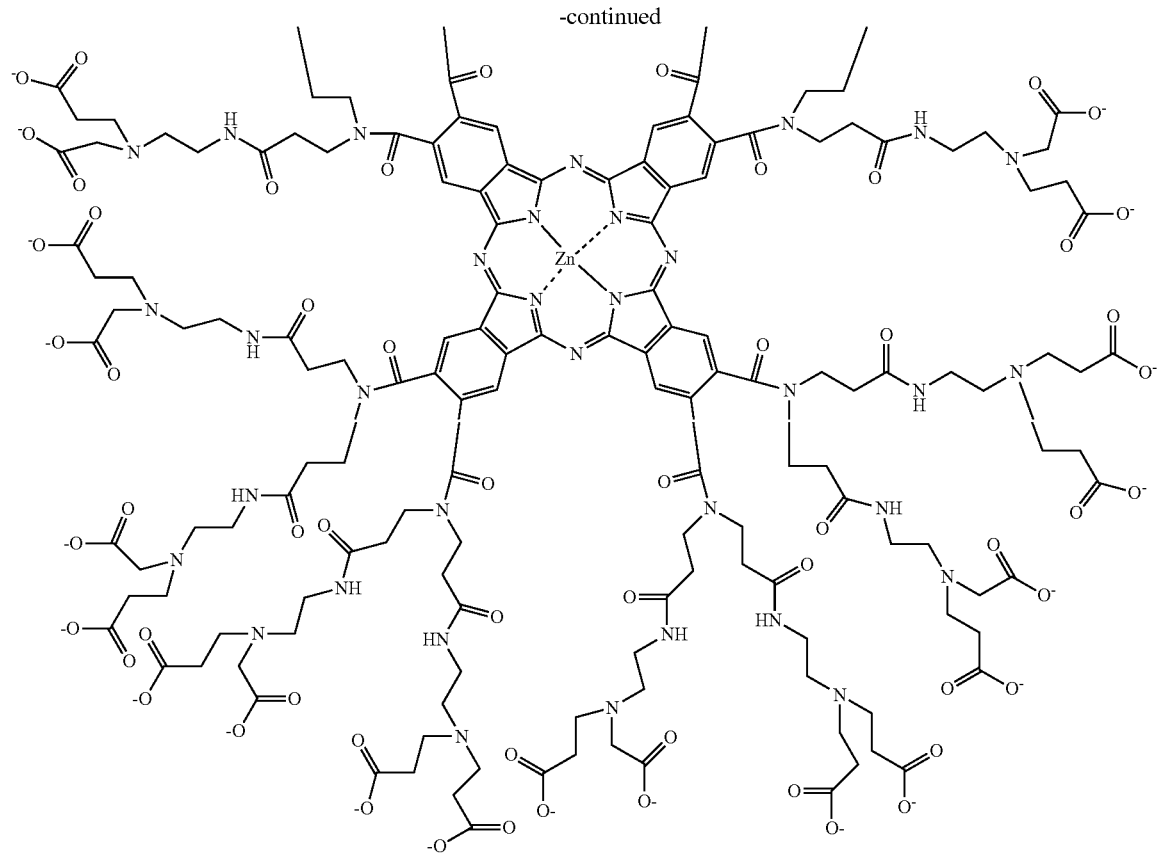

Table 1 shows data on UV-Vis, fluorescence, and ESR spectra of the raw material compounds and the compounds of the present invention.

TABLE 1

| Compound | λmax | log ε | Fmax | g value |
|---|---|---|---|---|
| $H_2$—PC | 687.50 | 2.4647 | 625 | 1.9712 |
|  | 654.00 | 2.0593 | 700 | 2.0245 |
|  | 624.50 | 2.0332 |  |  |
| Zn—PC | 655.50 | 4.5813 | 715 | 1.9712 |
|  | 607.00 | 4.5391 |  | 2.0245 |
| Zn—PC tetracarboxylic acid | 772.50 | 4.2177 | 805 | 1.9713 |
|  | 690.50 | 3.5958 |  | 2.0245 |
| Zn—PC octacarboxylic acid | 769.00 | 4.2560 | 780 | 1.9713 |
|  | 747.00 | 4.2054 |  | 2.0245 |
| G-1.0 dendritic Zn—PC | 762.00 | 7.6081 | 780 | 1.9713 |
|  | 733.50 | 7.5915 |  | 2.0245 |

FIG. 1 shows a fluorescence spectrum of the above-obtained G1.0 dendritic PC.

As is clear from Table 1, each of the phthalocyanine moieties or the dendritic PC of the present invention exhibits an absorption maximum wavelength at more than 650 nm, indicating that the dendritic PC is suitable for photodynamic therapy. As is also clear from Table 1, the dendritic PC of the present invention has a function as an optical material (i.e., an optical function up to a near-infrared region), and the dendritic PC emits fluorescence; i.e., the dendritic PC exhibits characteristics for photodynamic therapy. Also, the data on g value indicate that the dendritic PC generates radicals.

As is clear from FIG. 1, the dendritic PC of the present invention, although having a dendritic moiety, emits fluorescence with a small Stokes' shift, and thus the dendritic PC exhibits characteristics for photodynamic therapy.

Example 2

Studies were conducted on the effect of the dendritic PC of the present invention on IU-002 cells, which are rhesus-derived cancer cells.

IU-002 cells were incubated at 37° C. in the presence of the dendritic PC of different concentrations. After three-hour incubation, the dendritic PC concentration of IU-002 cells was measured. The degree of incorporation of the dendritic PC into cells was found to increase in accordance with an increase in dendritic PC concentration.

In general, phthalocyanines are likely to aggregate, and the thus-aggregated phthalocyanines do not act as a photosensitizer (J. Phys. Chem., 96 (1992), 8832-8839). In addition, the aggregated phthalocyanines do not emit fluorescence.

In contrast, the dendritic PC of the present invention emitted fluorescence in IU-002 cells.

Figure 2:
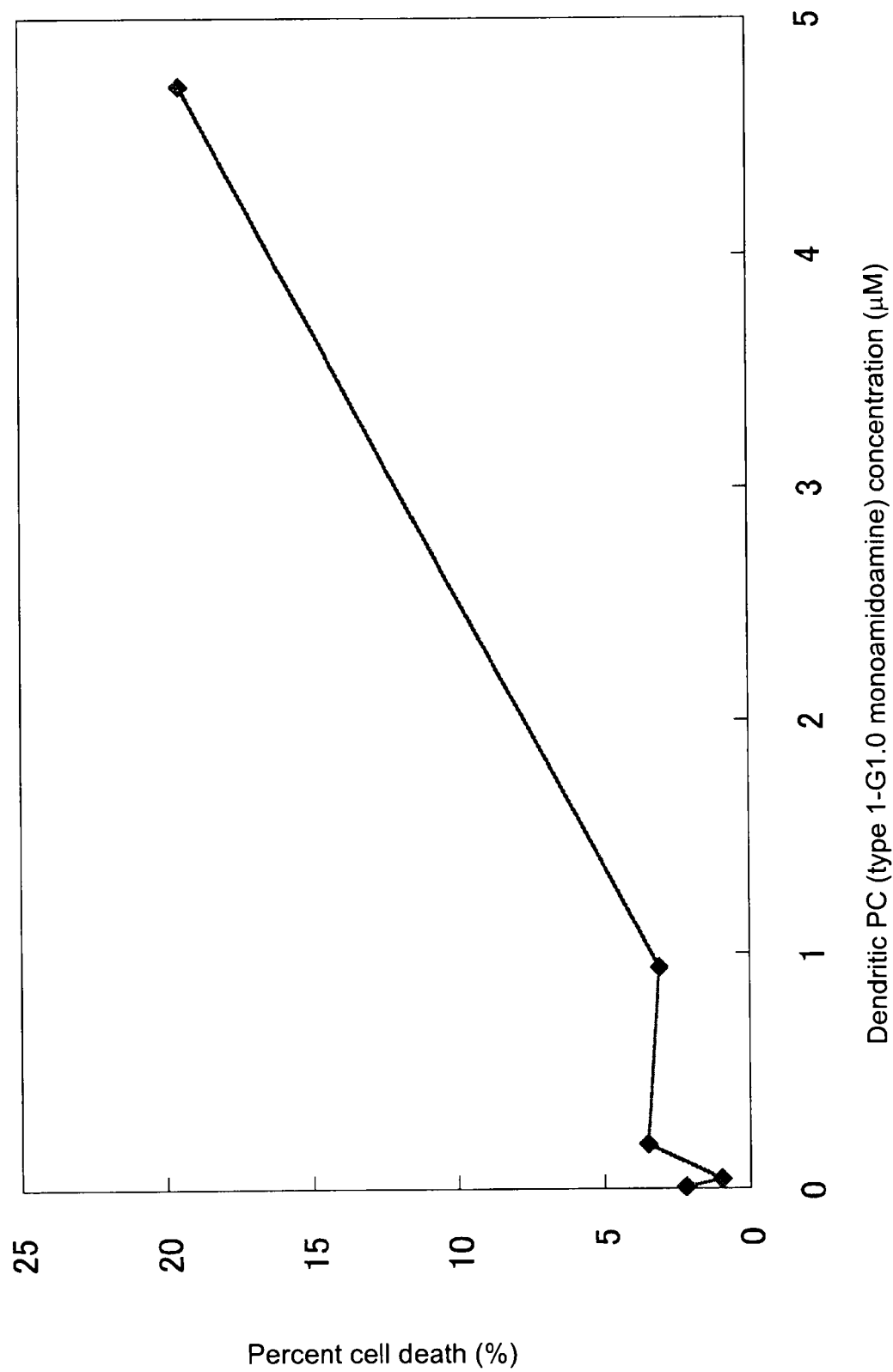
FIG. 2 shows the percent death (%) of IU-002 cells into which dendritic PC (type 1-G1.0 monoamidoamine) has been incorporated.
Figure 3:
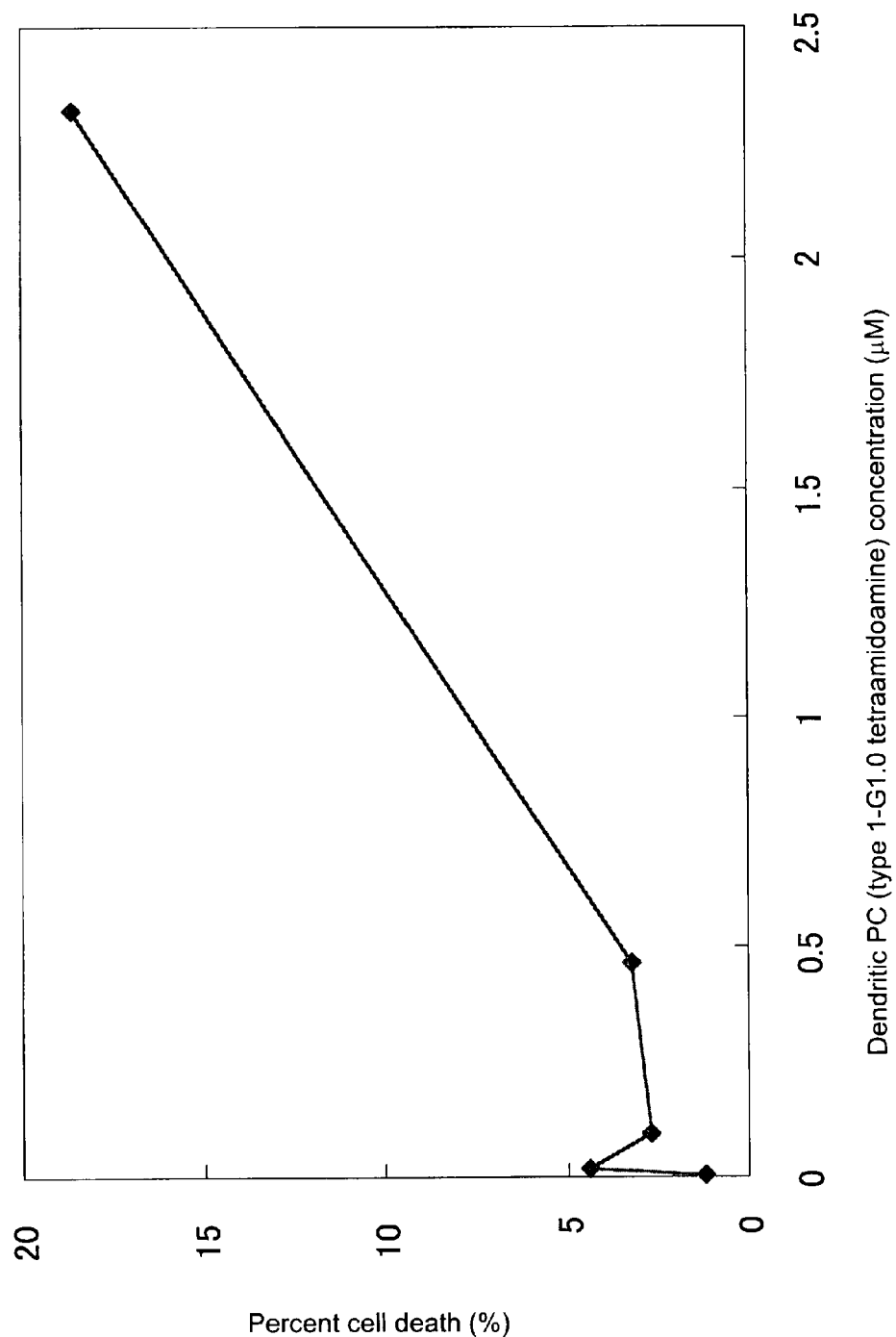
FIG. 3 shows the percent death (%) of IU-002 cells into which dendritic PC (type 1-G1.0 tetraamidoamine) has been incorporated.
Figure 4:
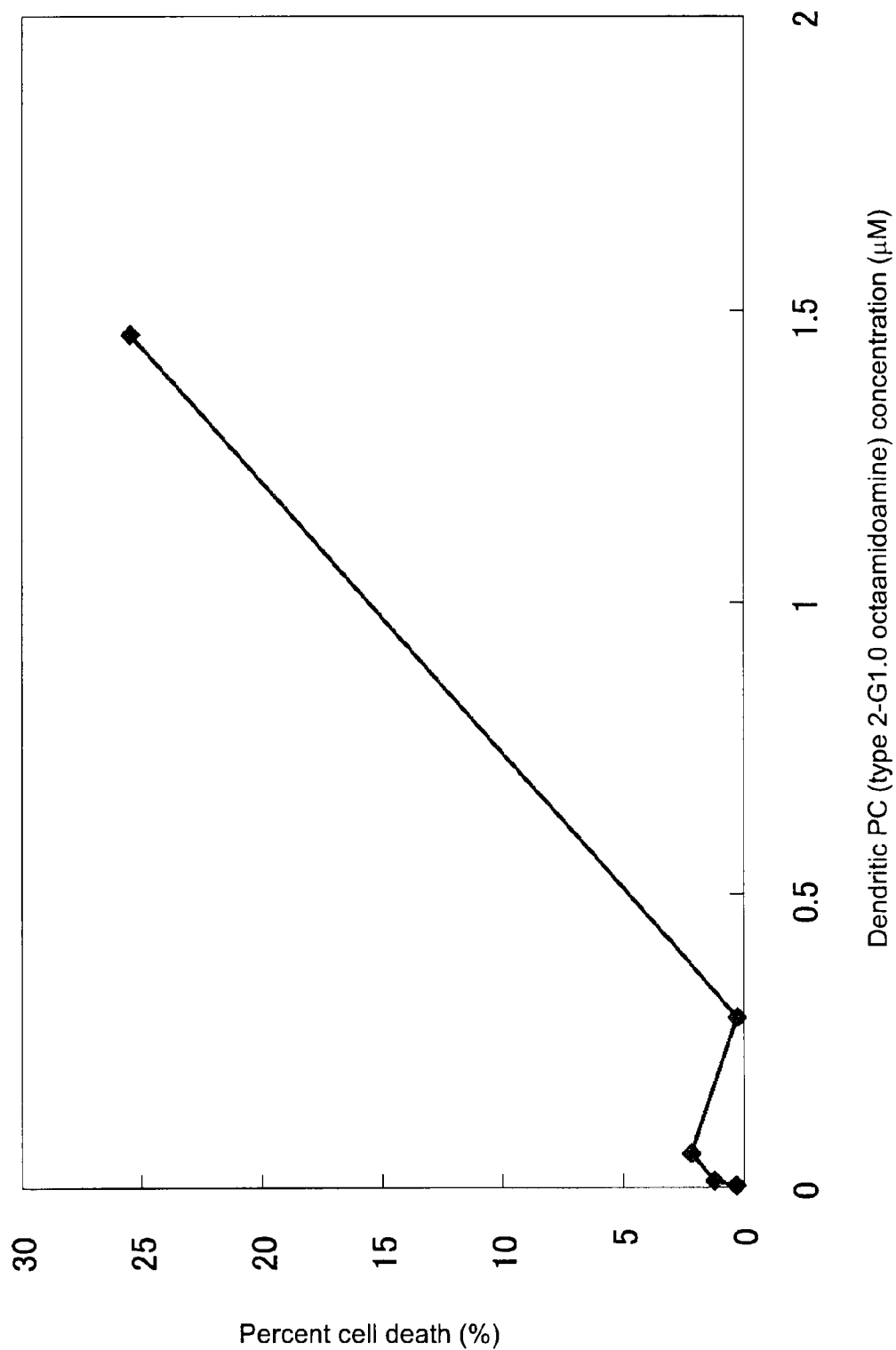
FIG. 4 shows the percent death (%) of IU-002 cells into which dendritic PC (type 2-G1.0 octaamidoamine) has been incorporated.

IU-002 cells into which the dendritic PC of the present invention had been incorporated were irradiated with halogen light for 10 minutes. As a result, the percent death of IU-002 cells was found to increase in a dendritic PC concentration-dependent manner (FIGS. 2 to 4). In contrast, the percent death of non-light-irradiated cells did not increase.

These data indicate that the dendritic PC of the present invention is useful as a photodynamic therapeutic drug for cancer.

The invention claimed is:

1. A dendritic polyamidoamine phthalocyanine represented by the following formula (1):

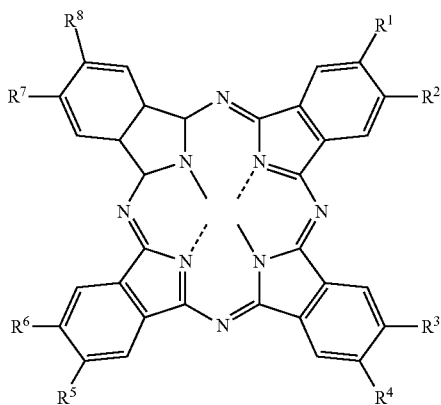

(wherein 1 to 8 among $R^1$ to $R^8$ are respectively polyamidoamine dendron represented by the following formula (a):

[F2]

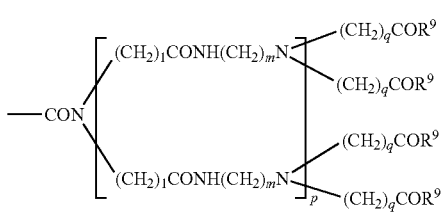

(wherein p is a number from 1 to 4; $R^9$ represents —NH$(CH_2)_t$NH$_2$ or $OR^{10}$ (wherein $R^{10}$ represents an alkyl group); and each of l, m, q, and t is a number from 1 to 8), and the remaining member(s) represent(s) a hydrogen atom; M represents a metal atom having a valency of two or more; and the ring X is a benzene ring, a pyridine ring, or a pyrazine ring).

2. A phthalocyanine compound according to claim 1, wherein each member of four or eight of $R^1$ to $R^8$ is a dendron represented by formula (a).

3. A phthalocyanine compound according to claim 1, wherein p is a number of 1 to 3.

4. A phthalocyanine compound according to claim 2, wherein p is a number of 1 to 3.

5. A fluorescent material comprising a phthalocyanine compound according to claim 1.

6. A fluorescent material comprising a phthalocyanine compound according to claim 2.

7. A fluorescent material comprising a phthalocyanine compound according to claim 3.

8. A pharmaceutical composition comprising a phthalocyanine compound according to claim 1 and a pharmaceutically acceptable carrier.

9. A pharmaceutical composition comprising a phthalocyanine compound according to claim 2 and a pharmaceutically acceptable carrier.

10. A pharmaceutical composition comprising a phthalocyanine compound according to claim 3 and a pharmaceutically acceptable carrier.

11. A method of photodynamic therapy treating a subject for cancer, comprising administering, to the subject in need thereof, an effective amount of a phthalocyanine compound according to claim 1.

12. A method of photodynamic therapy treating a subject for cancer, comprising administering, to the subject in need thereof, an effective amount of a phthalocyanine compound according to claim 2.

13. A method of photodynamic therapy treating a subject for cancer, comprising administering, to the subject in need thereof, an effective amount of a phthalocyanine compound according to claim 3.

14. A method of preparing a therapeutic drug for the photodynamic therapy treatment of cancer, comprising:
formulating a mixture of a therapeutically effective amount of the phthalocyanine compound according to claim 1 and pharmaceutically acceptable excipients.

15. A method of preparing a therapeutic drug for the photodynamic therapy treatment of cancer, comprising:
formulating a mixture of a therapeutically effective amount of the phthalocyanine compound according to claim 2 and pharmaceutically acceptable excipients.

16. A method of preparing a therapeutic drug for the photodynamic therapy treatment of cancer, comprising:
formulating a mixture of a therapeutically effective amount of the phthalocyanine compound according to claim 3 and pharmaceutically acceptable excipients.

* * * * *

UNITED STATES PATENT AND TRADEMARK OFFICE
CERTIFICATE OF CORRECTION

PATENT NO. : 8,030,342 B2
APPLICATION NO. : 12/513075
DATED : October 4, 2011
INVENTOR(S) : Keiichi Sakamoto et al.

Page 1 of 2

It is certified that error appears in the above-identified patent and that said Letters Patent is hereby corrected as shown below:

Column 17, lines 5-22:

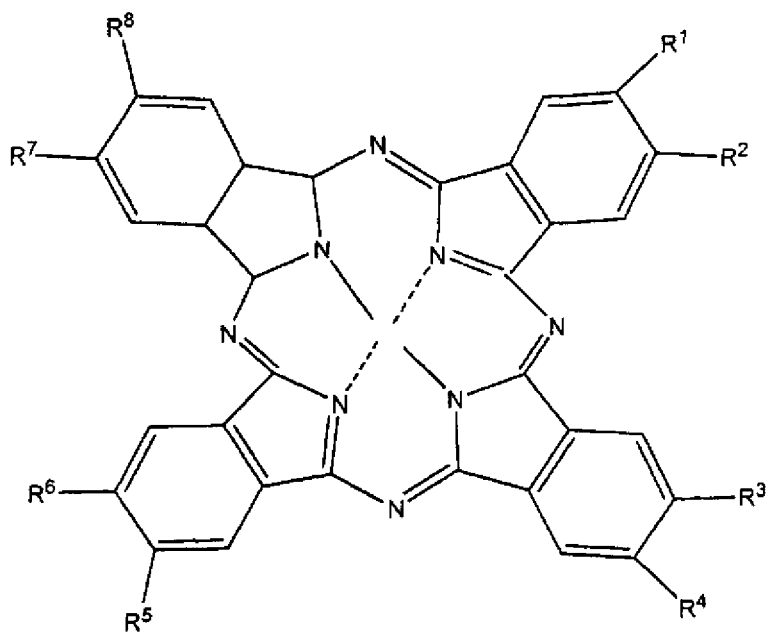

Signed and Sealed this
Thirteenth Day of December, 2011

David J. Kappos
*Director of the United States Patent and Trademark Office*

CERTIFICATE OF CORRECTION (continued)
U.S. Pat. No. 8,030,342 B2

Column 17, lines 5-22 (Continued)
Should read:

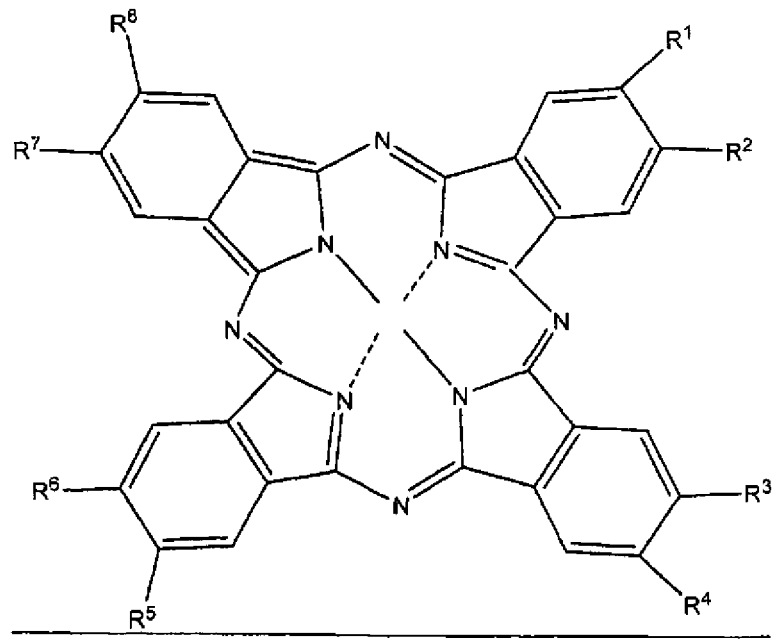

UNITED STATES PATENT AND TRADEMARK OFFICE
CERTIFICATE OF CORRECTION

PATENT NO. : 8,030,342 B2  
APPLICATION NO. : 12/513075  
DATED : October 4, 2011  
INVENTOR(S) : Keiichi Sakamoto et al.

Page 1 of 1

It is certified that error appears in the above-identified patent and that said Letters Patent is hereby corrected as shown below:

Column 17, lines 5-22:
Should read:

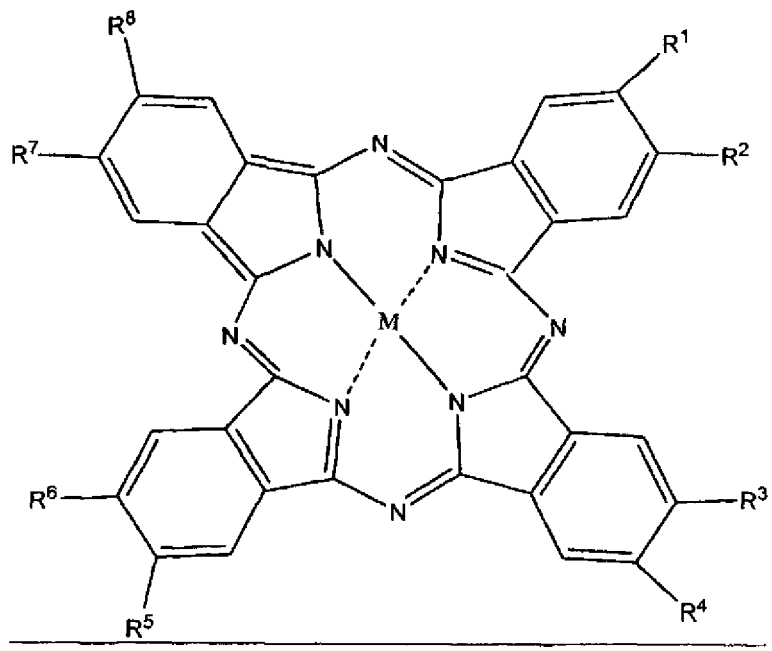

This certificate supersedes the Certificate of Correction issued December 13, 2011.

Signed and Sealed this
Seventeenth Day of April, 2012

David J. Kappos
*Director of the United States Patent and Trademark Office*